(12) United States Patent
Li et al.

(10) Patent No.: US 6,406,840 B1
(45) Date of Patent: Jun. 18, 2002

(54) CELL ARRAYS AND THE USES THEREOF

(75) Inventors: Ronghao Li, La Jolla; Jennie P. Mather, Millbrae, both of CA (US)

(73) Assignee: bioMosaic Systems, Inc., South San Francisco, CA (US)

( * ) Notice: Subject to any disclaimer, the term of this patent is extended or adjusted under 35 U.S.C. 154(b) by 0 days.

(21) Appl. No.: 09/466,011

(22) Filed: Dec. 17, 1999

(51) Int. Cl.$^7$ .............................. C12N 5/02; C12N 1/04
(52) U.S. Cl. ...................... 435/1.3; 435/325; 435/243
(58) Field of Search ........................... 435/287, 6, 7.1, 435/1.3, 325, 243; 530/333, 334, 25.3

(56) References Cited

U.S. PATENT DOCUMENTS

| | | | |
|---|---|---|---|
| 4,537,860 A | * 8/1985 | Tolbert | ........................ 435/240 |
| 5,143,854 A | 9/1992 | Pirrung et al. | |
| 5,324,591 A | 6/1994 | Georger, Jr. et al. | |
| 5,478,722 A | * 12/1995 | Caldwell | ..................... 435/1.1 |
| 5,763,263 A | * 6/1998 | Dehlinger | ................... 435/287 |

FOREIGN PATENT DOCUMENTS

| | | | |
|---|---|---|---|
| WO | WO 96/17246 | * | 6/1996 |
| WO | WO 97/45730 | | 12/1997 |
| WO | WO 98/38490 | | 9/1998 |
| WO | WO 99/13313 A1 | | 3/1999 |
| WO | WO 99/19711 A1 | | 4/1999 |
| WO | WO 99/44062 | | 9/1999 |
| WO | WO 99/44063 | | 9/1999 |
| WO | WO 99/55460 A1 | | 11/1999 |
| WO | WO 99/60170 | * | 11/1999 |
| WO | WO 01/09607 A1 | | 2/2001 |

OTHER PUBLICATIONS

Sugimoto (Journal of Osaka University Dental Society, 1974, 19/1, 130–140–abstract only).*

Smits (Journal of Urology, Jan. 1991, vol. 145, pp 171–175).*

Krawczyk (Analytical Biochemistry, Aug. 15, 1978 165(1), pp 20–7).*

Aplin et al. (1981). "Protein–Derivatised Glass Coverslips for the Study of Cell–to–Substratum Adhesion" *Anlaytical Biochem* 113:144–148.

Ausubel, et al. eds. (1995). *Current Protocols In Molecular Biology*. John Wiley & Sons, Table of Contents provided herewith.

Barnes and Sato. (1980). "Methods for Growth of Cultured Cells in Serum–Free Medium" *Analytical Biochem.* 102:255–270.

Cantley et al. (1991) "Oncogenes and Signal Transduction" *Cell* 64:281–302.

Freshney, R., ed. (1987). *Animal Cell Culture: a practical approach*. IRL Press: Oxford. Table of contents provided herewith.

Ham and McKeehan. (1979). "Media and Growth Requirements" *Methods in Enzymology* 58:44–93.

Harlow and Lane, eds. (1988) *Antibodies, A Laboratory Manual*. Cold Spring Harbor Laboratory: New York. Table of Contents provided herewith.

Humason, G. (1967). *Animal Tissue Techniques 2nd Ed.* W. H. Freeman & Company: London, pp 68–69.

Humason, G. (1967). *Animal Tissue Techniques 2nd Ed.* W. H. Freeman & Company: London, pp 132–134.

Humason, G. (1967). *Animal Tissue Techniques 2nd Ed.* W. H. Freeman & Company: London. Table of Contents provided herewith..

Jakoby and Pastan, eds. (1979). *Methods In Enzymology*. Academic Press, Inc: New York. Table of Contents provided herewith.

Liscovitch et al. (1994). "Lipid Second Messengers" *Cell* 77:329–334.

MacPherson et al., eds. (1995). *PCR 2: A Practical Approach*. IRL Press: Oxford. Table of Contents provided herewith.

Mannheim. *Nonradioative In Situ Hybridization Application Manual 2nd Ed.* Roche Molecular Biochemicals. Table of Contents provided herewith.

Mather, J.P. and Roberts, P.E. (1998). *Introduction to Cell and Tissue Culture: Theory and Technique*. Plenum Press: New York. Table of Contents provided herewith.

Mrksich et al. (1996). "Using Self–Assembled Monolayers to Understand the Interactions of Man–made Surfaces with Proteins and Cells" *Ann. Rev. Biophys. Biomol. Struct* 25:55–78.

Sambrook et al. (1989). *Molecular Cloning: A Laboratory Manual 2nd Ed.* Cold Spring Harbor Press: New York. Table of Contents provided herewith.

Sato et al., eds. (1982). *Growth of Cells in Hormonally Defined Media*. Cold Spring Harbor Press: New York. Table of Contents provided herewith.

* cited by examiner

*Primary Examiner*—John S. Brusca
(74) *Attorney, Agent, or Firm*—Morrison & Foerster LLP

(57) ABSTRACT

The present invention provides cell arrays comprising a plurality of tubes containing populations of cells that are immobilized therein. The arrays are particularly useful for conducting comparative cell-based analyses. Specifically, the subject arrays allow protein-protein interactions to be studied in multiple types of cell simultaneously. The arrays also support simultaneous detection of the differential expression of a target polynucleotide in a multiplicity of cell types derived from multiple subjects. The subject arrays further permit high throughput screening for candidate modulators of a signal transduction pathway of interest. Further provided by the invention are kits, computer-implemented methods and systems for conducting the comparative cell-based analyses.

24 Claims, 2 Drawing Sheets

(1 of 2 Drawing Sheet(s) Filed in Color)

CELL ARRAYS AND THE USES THEREOF

TECHNICAL FIELD

This invention is in the field of cell biology. Specifically, the invention relates to the generation of a cell array comprising a multiplicity of cell types. Such array can be used to generate multiple test units containing cells of identical type and passage. The compositions and methods embodied in the present invention are particularly useful for rapid identification of differential gene expression patterns and protein-protein interaction patterns, as well as for high throughput screening of candidate modulators of signal transduction pathways.

BACKGROUND OF THE INVENTION

The imminent completion of sequences of the entire human genome will provide a wealth of information on gene sequences, and genome structure and organization. The acquisition of the genome sequences of multiple model organisms will further open up new avenues to search for the biological significance of these data. The next objective is to harness this vast wealth of genetic data in the prediction, diagnosis and treatment of diseases. In particular, methods are required which will allow one to distinguish differential gene expression patterns between cells of different organisms, between different cell types of the same organism, or between different pathological stages of the same cell. Additional techniques are needed for recordation and correlation of the temporal changes in cell physiology in response to a variety of external stimuli. Methods of this type are denoted "functional genomics", which aims at delineating the relationship between the phenotype of a cell with its genotype at any given time.

Delineating the genotypic characteristics contributing to the phenotypic traits of a given cell type has until now been a daunting task. Traditional approaches for identifying genes or gene products unique to a particular type of cell are generally highly limited, targeting at only one, or a few specific gene sequences, and analyzing one cell type at a time. This is primarily due to the fact that maintaining multiple cell lines or types of cell cultures is extremely costly and labor intensive. Recently developed techniques such as micro-patterned arrays (described in WO 97/45730, WO 98/38490) and microfluidic arrays provide valuable tools for comparative cell-based analysis, but they also have pronounced limitations. To the extent that these techniques employ living cells whose characteristics may not remain constant from one experiment to another, inherent variability associated with cells carried in different facilities or with varying passages is inevitably being introducing during experimentation. It is a well-known problem in the art that both genotypic and phenotypic characters of cells may change over time when cultured in vitro.

There thus remains a considerable need for devices and methods of performing comparative cell-based analyses with minimum inconsistencies. An ideal device would allow (a) the cellular activities of multiple types of cells to be examined simultaneously; (b) the same batches of cells of multiple types to be tested during multiple rounds of experiments, so as to minimize the variability in cell conditions; and finally, the devices must support high throughput screening for candidate therapeutic targets and/or agents in a cost effective fashion. The present invention satisfies these needs and provides related advantages as well.

SUMMARY OF THE INVENTION

A principal aspect of the present invention is the design of a technique capable of generating multiple copies of a miniaturized cell array comprising a variety of cell types. This technique of cell-array production simplifies the laborious and expensive procedures of culturing multiple types of cells each time when needed. This technique allows multiple rounds of biological assays, or assays carried out at different facilities in different geographical locations, to be conducted on cells having essentially the same characteristics as those used in a previous experiment, and thus minimizes experimental variations in cell conditions often encountered when dealing with cells of different batches, varying passages, and of different laboratory or depository origin.

Accordingly, the present invention provides a method of preparing a cell array that comprises the following steps: (a) providing an array of tubes, each tube having at least one lumen and a population of cells that is contained within said lumen; (b) cross-sectioning the array of tubes to yield a plurality of transverse tube segments; and (c) immobilizing the plurality of tube segments on a solid support.

The present invention also provides a tube having a maximum length in the range of about 0.01 micron to about 5 mm. The tube has at least one lumen and a population of cells that is contained and immobilized within the lumen. In one aspect of this embodiment, the tube has a transverse sectional area of about 0.01 $mm^2$ to about 5 $cm^2$. In another aspect, the tube is made of one or more substances selected from the group consisting of plastic polymer, glass, cellulose, nitrocellulose, semi-conducting materials, and metal. In yet another aspect, the tube contains a population of cells that is embedded in a matrix. The matrix can be made of one or more of the substances selected from the group consisting of methocellulose, laminin, fibronectin, collagen, agar, Matrix-gel®, OCT compound, and paraffin.

In a separate aspect of this embodiment, the population of cells contained in the tube is substantially homogenous. The cells can be living or dead cells; eukaryotic or prokaryotic cells; embryonic or adult cells; or cells of ectodermal, endodermal or mesodermal origin. The cells loaded in the tube can also be freshly isolated cells, cultured cells in either primary or secondary cultures, or cells of an established cell line. Furthermore, the cells may be wildtype, genetically altered or chemically treated cells.

The present invention further provides a cell array comprising a plurality of the tubes embodied in the invention. In one aspect of this embodiment, each tube of the cell array is immobilized on a solid support. The solid support on which tubes of cells are arrayed can be flexible or rigid. Preferably, the solid support is made of plastic polymer, glass, cellulose, nitrocellulose, semi-conducting material, metal, or any combination thereof. A preferred cell array comprises at least two tubes having an exposed upper transverse sectional surface. Optionally, polynucleotides contained in the tubes of cells are denatured.

In another aspect, at least a subset of the tubes in the cell array comprises cells of a unique type. The tubes in the subset may have multiple lumens, wherein each lumen of the tube within the subset contains a cell population that is unique with respect to all other cell populations contained in other lumens of the tubes of the subset. In an alternative, the tubes in the subset may have multiple lumens, wherein each lumen of the tube within the subset contains a cell population that is unique with respect to all other cell populations contained in other lumens of the same tube. Each tube of a cell array may contain at least 10 cells of the same type, preferably 100 cells of the same type. The cell array may optionally contain tubes of control cells.

In a separate aspect of this embodiment, the cells contained in the tubes of the subset of tubes differ in one or more of the characteristics selected from the group consisting of genotypic characteristics, species origin, developmental stage, developmental origin, tissue origin, cell-cycle point, chemical treatment and disease state. Whereas the species origin may be selected from the group consisting of human, mouse, rat, fruit fly, worm, yeast and bacterium, suitable tissues from which cells are derived are blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The cells contained in the subset of tubes of the array may also differ in developmental stage including embryo and adult stages, as well as developmental origin such as ecotodermal, mesodermal, and ectodermal origin. As such, the invention cell arrays encompass embryonic cell arrays, adult cell arrays, primary cell arrays, cell line arrays, tissue arrays, mammalian cell arrays, zoo arrays, personal cell arrays, genetically altered cell arrays, chemically treated cell arrays, and disease cell arrays. A preferred disease cell array is a cancer cell array.

Also provided in the present invention are methods of using the above described cell arrays. In one embodiment, the present invention provides a method of simultaneously detecting the presence of a specific protein-protein interaction involving a proteinaceous probe and a target protein in multiple types of cells. The method involves the steps of: (a) providing a subject cell array; (b) contacting a proteinaceous probe that is specific for a target protein with the array of tubes under conditions sufficient to produce a stable probe-target complex; and (c) detecting the formation of the stable probe-target complex in each tube, thereby detecting the presence of specific protein-protein interaction in multiple types of cells. Examples of proteinaceous probes that may be employed in the assay are antibodies, cell surface receptors, secreted proteins, receptor ligands, immunoliposomes, immunotoxins, cytosolic proteins, nuclear proteins, and functional motifs thereof. Examples of target proteins that may be detected are membrane proteins, secreted proteins, cytosolic proteins, nuclear proteins and chaperon proteins. In certain aspects, the target protein is differentially expressed in one or more cell types contained in the array of tubes.

In another embodiment, the present invention provides a method of determining cell-type binding selectivity of an antibody using the cell arrays.

In yet another embodiment, the present invention provides a method of detecting differential expression of a target protein in a multiplicity of cell types derived from at least two subjects. Such method involves: (a) staining a first cell array of claim 16 with an antibody that is specific for the target protein, wherein the array comprises a plurality of tubes containing a multiplicity of cell types of a first subject; (b) detecting the stain in each tube of the array that forms a first immunostaining pattern representative of the differential expression of said target in the multiple types of cells of the first subject; (c) staining a second cell array of claim 16 with an antibody that is specific for the target protein, wherein the array comprises a plurality of tubes containing a multiplicity of cell types of a second subject; (d) detecting the stain in each tube of the second array that forms a second immunostaining pattern representative of the differential expression of said target in the multiple types of cells of the second subject; and (e) comparing the immunostaining patterns, thereby detecting the differential expression of the target protein in the multiplicity of cell types of the subjects.

In yet another embodiment, the invention provides a method of detecting differential representation of a target polynucleotide in a multiplicity of cell types.

In yet another embodiment, the invention provides a method of detecting differential representation of a target polynucleotide in a multiplicity of cell types derived from at least two subjects.

In yet still another embodiment, the invention includes a method for identifying a modulator of a signal transduction pathway. Such method comprises the steps of (a) providing a cell array as described above, wherein at least a subset of the tubes on the array contains cells expressing at least one reporter molecule that yields a detectable signal transduction readout; (b) contacting the array with a candidate modulator; and (c) assaying for a change in the signal transduction readout, thereby identifying a modulator of the signal transduction pathway.

In addition, the invention encompasses computer-implemented methods for detecting differential expression of a target polynucleotide or protein in a multiplicity of cell types. Also included are computer-based systems for detecting differential expression of a target polynucleotide or protein in a multiplicity of cell types derived from at least two subjects. Further provided by the present invention are kits for simultaneously detecting the presence of a target polynucleotide or polypeptide in a multiplicity of cell types comprising the subject cell arrays in suitable packaging.

BRIEF DESCRIPTION OF THE DRAWINGS

The file of this patent contains at least one drawing executed in color. Copies of this patent with color drawings are provided to the Patent and Trademark Office with payment of the necessary fee.

MODES FOR CARRYING OUT THE INVENTION

Figure 1:
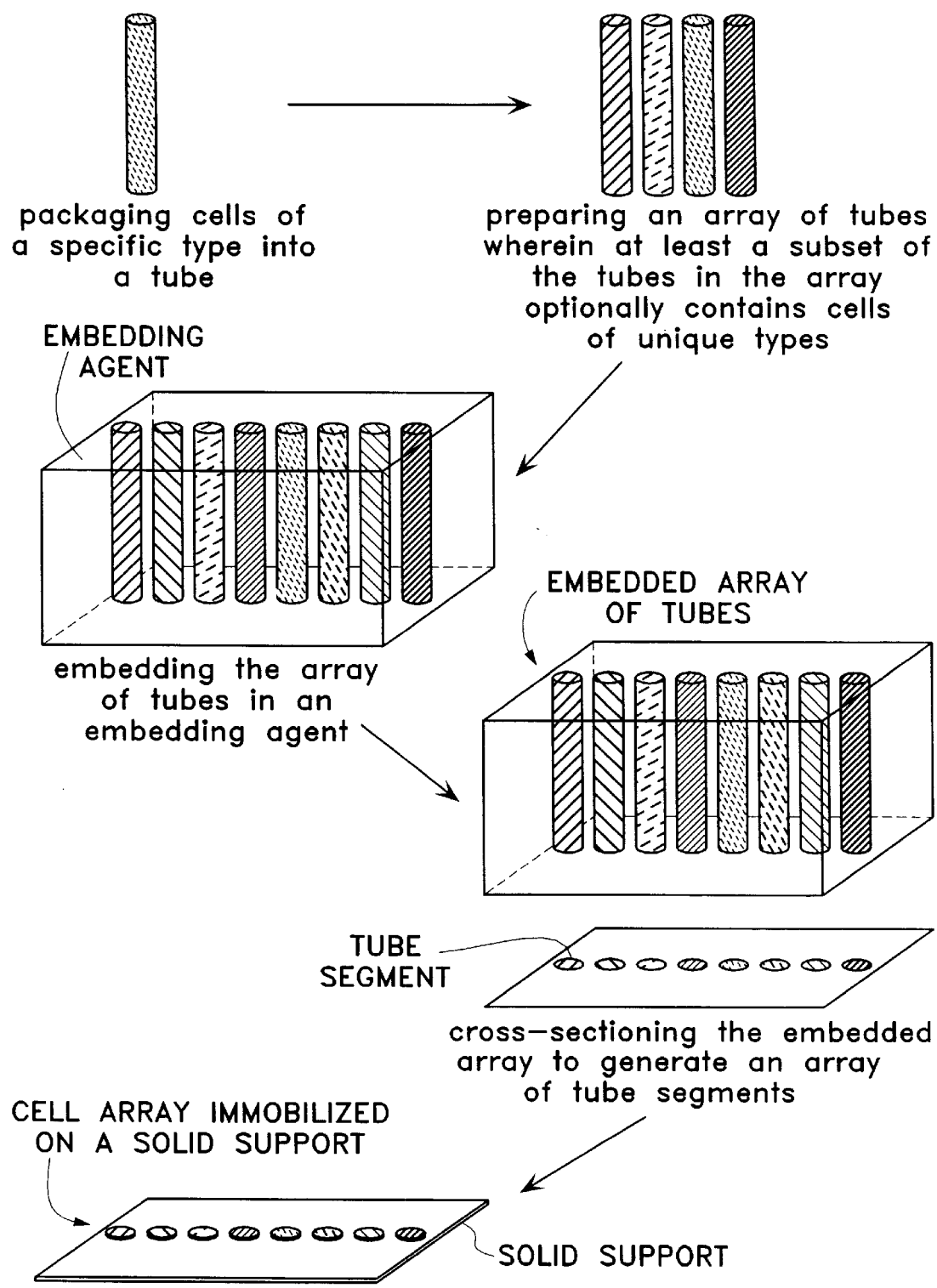
FIG. 1 depicts an exemplary process for preparing a cell array of the present invention.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The terms "polynucleotide", "nucleotide" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" refers to a polynucleotide used for detecting or identifying its corresponding target polynucleotide in a hybridization reaction.

"Operably linked" or "operatively linked" refers to ajuxtaposition wherein the components so described are in a relationship permitting them to function in their intended manner. For instance, a promoter sequence is operably linked to a coding sequence if the promoter sequence promotes transcription of the coding sequence.

A "gene" refers to a polynucleotide containing at least one open reading frame that is capable of encoding a particular protein after being transcribed and translated.

"Genes of a specific developmental origin" refer to genes expressed at certain but not all developmental stages. For instance, a gene may be of embryonic or adult origin depending on the stage during which the gene is expressed.

A cell is of "ectodermal", "endodermal" or "mesodomal" origin, if the cell is derived, respectively, from one of the three germ layers—the ectoderm, the endoderm, or the mesoderm of an embryo. The ectoderm is the outer layer that produces the cells of the epidermis and the nervous system. The endoderm is the inner layer that produces the lining of the digestive tube and its associated organs, including but not limited to pancreas and liver. The middle layer, mesoderm, gives rise to several organs (including but not limited to the heart, kidney, and gonads), connective tissues (e.g., bone, muscles, and tendons), and the blood cells.

A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Different polynucleotides are said to "correspond" to each other if one is ultimately derived from another. For example, a sense strand corresponds to the anti-sense strand of the same double-stranded sequence. mRNA (also known as gene transcript) corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. A polynucleotide may be said to correspond to a target polynucleotide even when it contains a contiguous portion of the sequence that share substantial sequence homology with the target sequence when optimally aligned.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product". If the polynucleotide is derived from genomic DNA, expression may include splicing of the mRNA in an eukaryotic cell.

"Differentially expressed", as applied to nucleotide sequence or polypeptide sequence in a subject, refers to over-expression or under-expression of that sequence when compared to that detected in a control. Underexpression also encompasses absence of expression of a particular sequence as evidenced by the absence of detectable expression in a test subject when compared to a control.

"Differential expression" or "differential representation" refers to alterations in the abundance or the expression pattern of a gene product. An alteration in "expression pattern" may be indicated by a change in tissue distribution, or a change in hybridization pattern reviewed on an array of the present invention.

The term "hybridize" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"In situ hybridization" is a well-established technique that allows specific polynucleotide sequences to be detected in morphologically preserved chromosomes, cells or tissue sections. In combination with immunocytochemistry, in situ hybridization can relate microscopic topological information to gene activity at the DNA, mRNA and protein level.

"Signal transduction" is a process during which stimulatory or inhibitory signals are transmitted into and within a cell to elicit an intracellular response. A "modulator of a signal transduction pathway" refers to a compound which modulates the activity of one or more cellular proteins mapped to the same specific signal transduction pathway. A modulator may augment or suppress the activity of a signaling molecule.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "ligand" refers to a molecule capable of being bound by the ligand-binding domain of a receptor. The molecule may be chemically synthesized or may occur in nature. A ligand may be an "agonist" capable of stimulating the biological activity of a receptor, or an "antagonist" that inhibits the biological activity of a receptor.

"Proteinaceous probe" is a polypeptide-containing molecule that identifies a target protein by specifically binding to the target protein to form a stable target-probe complex. Non limiting representative proteinaceous probes are antibodies, immunoliposomes, and immunotoxins that specifically interact with their respective cellular targets.

"Cell surface receptors" or "surface antigens" are molecules anchored on the cell plasma membrane. They constitute a large family of proteins, glycoproteins, polysaccharides and lipids, which serve not only as structural constituents of the plasma membrane, but also as regulatory elements governing a variety of biological functions.

As used herein, "membrane proteins" include peripheral and integral membrane polypeptides that are bound to any cellular membranes including plasma membranes and membranes of intracellular organelles.

The terms "cytosolic", "nuclear" and "secreted" as applied to cellular proteins specify the extracellular and/or subcellular location in which the cellular protein is mostly localized. Certain proteins are "chaperons", capable of translocating back and forth between the cytosol and the nucleus of a cell.

The term "OCT compound" refers to the chemical formulation that facilitates cutting and handling of frozen sections. It is a compound commonly known and widely employed by artisans in the field of histochemistry. Typically, OCT compounds, such as those manufactured by Lab-Tek Instruments Co., Westmont Ill., come in three types for three ranges of temperature, −10° C. to −20° C., −20° C. to −35° C., and −35° C. to −50° C. (see Animal Tissue Techniques, G. L Humason (1967) W. H. Freeman & Company at pages 68–69 for more details).

The term "functional motifs" as applied to proteinaceous probes of the present invention, refers to portions of the probes that are sufficient for a specific detection of the cellular target(s) to which the functional motifs bind. Thus, the functional motifs of an antibody encompass antibody fragments exhibiting comparable target binding specificity. Likewise, the functional motifs of an immunoliposome encompass components of the immunoliposome that retain the target binding specificity.

A "database" is a collection of data which share some common characteristics. For instance, a hybridization database comprises sets of hybridization patterns generated by contacting nucleotide probes with a cell array of the subject invention. Similarly, an immunostain database contains immunostaining patterns generated by contacting selected antibodies with the subject cell arrays.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

An "antigen" as used herein means a substance that is recognized and bound specifically by an antibody, a fragment thereof or by a T cell antigen receptor. Antigens can include peptides, proteins, glycoproteins, polysaccharides and lipids; portions thereof and combinations thereof. The antigens can be those found in nature or can be synthetic. They may be present on the surface or located within a cell.

A "subject" as used herein refers to a biological entity containing expressed genetic materials. The biological entity is preferably a vertebrate, preferably a mammal, more preferably a human. Tissues, cells and their progeny of a biological entity obtained in vivo or cultured in vitro are also encompassed.

A "control" is an alternative subject or sample used in an experiment for comparison purposes. A control can be "positive" or "negative". For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease).

A "tube" as used herein refers to a container having at least one lumen suitable for cell packaging, storage and preparation of the cell arrays of the present invention. The term encompasses all tubular structures, transverse segments of such tubular structures, which can be of variable size, shape, and volume. It is not intended to be limited as regard to the material from which and the manner in which it is made. A tube has a longitudinal axis substantially parallel with the wall of a tube, and a horizontal axis, along which transverse segments of a tube can be sectioned. The longitudinal axis may be the same length, or longer or shorter than the horizontal axis. The transverse segments of a tube may also vary in shape, length (also referred to as "height" and "vertical thickness"). A tube may be open on both ends, on either end, or closed. A tube may also contain more than one lumens.

Cells are contained and "immobilized" within one or more lumens of a tube when the mobility of cells is restricted by the tube wall and/or, preferably, by immobilizing matrix in which the cells are embedded.

Structure of the Cell Arrays of the Present Invention

A central aspect of the present invention is the design of a miniaturized cell array applicable for simultaneous detection of target polynucleotides or proteins in multiple types of cells. Distinguished from the previously described non-encapsulated cell arrays, the invention cell array comprises a plurality of tubes, wherein each tube has at least one lumen containing a population of cells of a specific type. In one aspect, the tubes have a maximum length of about 0.01 micron to about 5 mm, preferably of about 0.1 micron to about I mm, more preferably of about 1 micron to about 0.1 mm. In another aspect, the tubes are immobilized on a solid support. In a preferred embodiment, a subset of the array of tubes comprises at least two tubes, each tube of the subset containing cells of a unique type. In another preferred embodiment, the subset of tubes has multiple lumens, wherein each lumen of a tube within the subset contains a cell population that is unique with respect to all other cell populations contained in other lumens of the tubes of the whole subset. In yet another preferred embodiment, the subset of tubes has multiple lumens, wherein each lumen of a tube within the subset contains a cell population that is unique with respect to all other cell populations contained in other lumens of the same tube.

Several factors apply to the design of cell arrays having one or more of the above-mentioned characteristics. First, tubes of cells are stably associated with the surface of a solid support. By "stably associated" is meant that the tube segments containing cells of desired type maintain their position relative to the solid support under subsequent cell-based analyses including but are not limited to hybridization and immunostaining.

A second consideration of designing the cell array is to ensure that multiple copies of the same array can be generated at any time. This can be achieved by first packing a slurry of cells into a tube, followed by cross-sectioning the tube to yield transverse segments of tubes containing cells of the same type and from the same batch. As such, tubes of the present invention must be divisible. Whereas the tubes may be made in any convenient shape, length, or size, they typically have a transverse sectional area in the range of about 0.1 mm$^2$ to about 5 cm$^2$. The transverse sectional area may be circular, elliptoid, oval, rectangular, triangular, polyhedral, or in any other analogously curved shape. The transverse area of each segment of a tube may also vary in size and shape.

A further consideration of designing the subject cell array is that each tube of the array comprises a substantially homogenous population of cells of the same type. A "substantially homogenous" cell population refers to a mixture of cells in which the type of cells of interest constitutes more than about 75% of the total number of cells. Preferably, the desired cells constitute more then 80%, more preferably 90%, and even more preferably more than 95% of the total number of cells. The types of cells on the array are dependent on the intended purpose of the cell array. For example, where the purpose is to examine the differential expression of a gene or a gene product in various organisms, each tube presented on the array comprises cells that are representative of a distinct organism to be tested. Any cells that are isolated from the test organism, whether they are cultured in vitro as primary culture or cell lines, or isolated from different tissues of that organism, can be immobilized in a single tube as they share a common characteristic, and hence are considered to be the same type. Where the purpose is to determine the tissue distribution pattern of a particular gene or a gene product, each tube may contain cells derived from a single tissue that is under investigation. Depending on the intended purpose of the cell array, cells may be considered to be the same type if they share some common characteristics including but not limited to species of origin, developmental origin, tissue origin, chemical treatment and/or cell cycle point.

Whereas cells within a tube lumen must be of the same type, at least a subset of the tubes in the cell array may contain unique tubes, each representing a unique cell type. As used herein, a "unique" cell type is distinct or different with respect to every other cell type presented by the entire, or the subset of tubes of concern. For instance, the cell array may comprise multiple tubes, each containing cells of a specific type that is different from those contained in all other tubes. In another example, the array comprises tubes having multiple lumens, wherein each lumen contains a unique cell type with respect to all other lumens of the same tube, or that of all other tubes of the same array. The unique cell type can be distinguished by one or more of the following features: genotype, species origin, developmental stage, developmental origin, tissue origin, cell-cycle point, chemcial treatment, and disease state. The percentage of tubes containing unique types of cells is generally at least about 25% of all other tubes of the array, preferably at least about 50%, more preferably at least about 75%, more preferably at least about 80%, and even more preferably at least about 90%. As such, the cell arrays of the subject invention encompass a variety of specific types of arrays. Representative array types include zoo array, mammalian cell array, human array, tissue array, primary cell array, cell line array, embryonic cell array, adult cell array, disease cell array, genetically-altered cell array, chemically-treated cell array, and the like. Each of these exemplary arrays is detailed below.

The "zoo array" of the subject invention comprises multiple unique tubes of cells, each tube corresponding to a distinct biological organism. Exemplary organisms include members of the plant or animal kingdom, and microorganisms such as viruses, bacteria, protozoa, and yeast. The "zoo array" may comprise cells of a unicellular or a multi-cellular organism. Preferably, the "zoo array" contains cells of a human being. More preferably, it contains cells of a model organism including but not limited to mouse, rat, fruit fly, worm, yeast, bacteria, corn and rice.

The "mammalian cell array" contains a plurality of unique tubes, each containing cells derived from a distinct mammal. Non-limiting examples of mammals are primates (e.g. chimpanzees and humans), cetaceans (e.g. whales and dolphins), chiropterans (e.g. bats), perrisodactyls (e.g. horses and rhinoceroses), rodents (e.g. rats), and certain kinds of insectivores such as shrews, moles and hedgehogs. One variation of this specific type of cell array is a "human array", in which the majority of the unique tubes of the array contain human cells of various types.

The "tissue array" embodied in the present invention comprises a plurality of unique tubes, each carrying a cell population representative of a specific body tissue from a subject. The types of body tissues include but are not limited to blood, muscle, nerve, brain, heart, lung, liver, pancreas, spleen, thymus, esophagus, stomach, intestine, kidney, testis, ovary, hair, skin, bone, breast, uterus, bladder, spinal cord and various kinds of body fluids. Non-limiting exemplary body fluids include urine, blood, spinal fluid, sinovial fluid, ammoniac fluid, cerebrospinal fluid (CSF), semen, and saliva.

Also embodied in the subject invention is a cell array having tubes of cells corresponding to different developmental stages (embryonic or adult) of an organism, or more specifically corresponding to various developmental origins including ectoderm, endoderm and mesoderm.

Further provided by the present invention is a cell array composed of tubes of freshly isolated cells, cells derived from a plurality of primary cultures (i.e. "primary cell array") or subcultures generated by expansion and/or cloning of primary culture (i.e. "cell line array"). Any cells capable of growth in culture can be used in preparation of this category of the invention cell arrays. Non-limiting examples of specific cell types that can now be grown in culture include connective tissue elements such as fibroblast, cells of skeletal tissue (bone and cartilage), cells of epithelial tissues (e.g. liver, lung, breast, skin, bladder and kidney), cardiac and smooth muscle cells, neural cells (glia and neurones), endocrine cells (adrenal, pituitary, pancreatic islet cells), melanocytes, and many different types of haemopoietic cells. Of particular interest is the type of cell that differentially expresses (over-expresses or under-expresses) a disease-causing gene. As is apparent to one skilled in the art, various cell lines may be obtained from public or private repositories. The largest depository agent is American Type Culture Collection (http://www.atcc.org), which offers a diverse collection of well-characterized cell lines derived from a vast number of organisms and tissue samples.

Another type of cell array embodied in the present invention is a "personal cell array", which comprises unique tubes of cells derived from individuals of a family, or individuals from different generations within the same pedigree. Cell arrays of this category are especially useful for forensic and parental identification.

Yet another type of invention cell array is one that comprises multiple unique cell tubes, each representing a type of cell that is associated with a particular disease or with a specific disease stage (i.e. "disease cell array"). The association with a particular disease or disease stage may be established by the cell's aberrant behavior in one or more biological processes such as cell cycle regulation, cell differentiation, apoptosis, chemotaxsis, cell motility and cytoskeletal rearrangement. A disease cell may also be confirmed by the presence of a pathogen causing the disease of concern (e.g. HIV for AIDS and HBV for hepatitis B). The types of diseases involving abnormal functioning of specific types of cells may include but are not limited to autoimmune diseases, cancer, obesity, hypertension, diabetes, neuronal and/or muscular degenerative diseases, cardiac diseases, endocrine disorders, and any combinations thereof.

Other categories of the subject arrays contain tubes of "genetically altered" or "chemically treated" cells. A cell is "genetically altered" as compared to a wildtype cell when a genetic element has been exogenously introduced into the cell other than by mitosis or meiosis. The element may be heterologous to the cell, or it may be an additional copy or improved version of an element already present in the cell. Genetic alteration may be effected, for example, by transfecting a cell with a recombinant plasmid, or other polynucleotide delivery vehicle through any process known in the art, such as electroporation, viral infection, calcium phosphate precipitation, or contacting with a polynucleotide-liposome complex. When referring to genetically altered cells, the term refers both to the originally altered cell, and to the progeny thereof. A preferred altered cell is one that carries a reporter gene to effect drug screening, cellular pathway delineation, and/or antibody selection.

A chemically treated cell array comprises unique tubes of cells, each being treated with distinct chemical agents or a particular combination of chemical agents. As used herein, a "chemical agent" is intended to include, but not be limited to a biological or chemical compound such as a simple or complex organic or inorganic molecule, a peptide, a protein (e.g. antibody), a polynucleotide (e.g. antisense oligonucleotide), a ribozyme and its derivative. A vast array of compounds can be synthesized, for example polymers, such as polypeptides and polynucleotides, and synthetic organic compounds based on various core structures, and these are also included in the term "chemical agent". In addition, various natural sources can provide compounds for screening, such as plant or animal extracts, and the like.

Where desired, the cell arrays of the present invention comprise controls, positive or negative, for comparison purposes. The selection of an appropriate control cells is dependent on the sample cells initially selected and/or the expression pattern of a gene or a gene product which is under investigation. One type of control cells serves as a positional marker for the orientation and positioning of the array. The tube itself or the cells within the tube may contain a detectable marker. The marker can be a colored dye, a luminescent molecule, a radioactive molecule, or a density or opacity marker. The positional controls containing these markers are particularly useful in positioning the array for reading the array results and storing data from the detection system. They may also be employed to align the array in an automated detection system and/or provide built in standards for calibrating and the detection system or normalizing data obtained from one cell array to another.

The control probes, whether nucleotide or proteinaceous, may also be classified into the following three categories: (a) normalization controls; (b) expression level control; and (c) mismatch controls.

Normalization controls serve to generate signals during in situ hybridization or immunostaining reactions as a control for variations in hybridization or staining conditions, label intensity, "reading" efficiency or any other factors that may cause the signal of a specific reaction to vary between arrays and among different regions of the same arrays. In a preferred embodiment, signals (e.g., fluorescence intensity) read from all other probes in the array are divided by the signal (e.g., fluorescence intensity) from the control probes thereby normalizing the measurements. Typically, the nucleotide normalization controls comprises sequences that are perfectly complementary to their respective target polynucleotides. Virtually any probe may serve as a normalization control. However, it is recognized that hybridization efficiency varies with base composition and probe length. Preferred normalization probes are selected to reflect the average length of the other probes present in the array. However, they can be selected to cover a range of lengths. The normalization control(s) can also be selected to reflect the base composition of the other probes in the array. A suitable proteinaceous probe may be one that binds to a ubiquitously expressed cellular protein.

Expression level controls are probes that hybridize or bind specifically to constitutively expressed genes or gene products in the cell array. Expression level controls are designed to control for the overall health and metabolic activity of a cell. Examination of the covariance of an expression level control with the expression level of the target polynucleotide or its protein product indicates whether measured changes or variations in expression level of a gene is due to changes in transcription or translation rate or to general variations in health of the cell. Thus, for example, when a cell is in poor health or lacking a critical metabolite the expression levels of both an active target gene and a constitutively expressed gene are expected to decrease. The converse is also true. Thus, where the expression levels of both an expression level control and the target gene or gene product appear to both decrease or to both increase, the change may be attributed to changes in the metabolic activity of the cell as a whole, not to differential expression of the target gene or its product in question. Conversely, where the expression levels of this target gene and the expression level control do not covary, the variation in the expression level of the target gene is attributed to differences in regulation of that gene and not to overall variations in the metabolic activity of the cell.

Any constitutively expressed gene and its product provides a suitable candidate for expression level control probes. Typically, expression level control probes have sequences encoding constitutively expressed "housekeeping proteins," which include, but are not limited to β-actin, transferrin receptor, GAPDH, and the like.

Mismatch probes provide a control for non-specific binding or cross-hybridization to a polynucleotide presented by other cells on the array than the target to which the probe is directed. Mismatch probes thus indicate whether a hybridization is specific or not. For example, if the target is present the perfect match probes should be consistently brighter than the mismatch probes. Typically, mismatch controls are polynucleotide probes identical to their corresponding target polynucleotide except for the presence of one or more mismatched bases. Mismatches are selected such that under appropriate hybridization conditions (e.g., stringent conditions) the test or control probe would be expected to hybridize with its target sequence, but the mismatch probe would not hybridize (or would hybridize to a significantly lesser extent). In general, as much as 20% base-pair mismatch (when optimally aligned) can be tolerated.

Preparation of the Subject Cell Array

The cell arrays of the present invention can be prepared by any means that yields a plurality of immobilized tubes of cells. Several factors apply to the design of a cell array preparation technique. First, the method must produce a cell array suited for large-scale, high throughput, cell-based assays. Second, the method must permit production of multiple copies of an array immobilized with identical batches of cells of, preferably distinct types. As such, the method of preparing the subject cell array supports repeated analyses of the same batches of cells, and avoid variability inevitably being introduced when new batches of cells of multiple types are required each time during a serial experimentation. A preferred method of preparation the subject cell microarrays involves the following steps: (a) providing an array of tubes, each tube having at least one lumen and a population of cells that is contained within said lumen; (b) cross-sectioning the array of tubes to yield a plurality of transverse tube segments; and (c) immobilizing the plurality of tube segments on a solid support.

Selection of tubes made of the subject array:

The tubes made up of the subject cell array have at least one lumen containing cells, preferably being immobilized therein. Also encompassed by the invention are tubes having multiple lumens, wherein some or all of the lumens are filled with cells of the same or distinct types. The lumens may take a variety of configurations. For instance, lumens within a cell container may be divided by linear walls to form separate but adjacent compartments, or by circular walls to form inner and outer annular compartments.

While tubes of the subject array may vary in size, shape, and volume, they must be made of divisible materials so that cross-sections of the tubes can be prepared. Preferably, the materials with which the tubes are fabricated also exhibit low level of non-specific activity during in situ hybridization or immunoassay. A variety of materials are suited for fabricating the subject tubes. They include a diversity of plastic polymers such as: polyamide (PA), polyimide (PI), polyacrylonitrile (PAN), polybutylene (PB), polybutadiene (PBD), polycaprolactam (PCL), polyethylene (PE), polychlorotrifluoroethylene (PCTFE), polytetrafluoroethylene (PTFE), polydimethylsiloxane (PDMS), polyethylene terephathalate (PET), polyisobutylene (PIB), polystyrene (PS), polyolefine (PO), polymeric polyisocyanate (PPI), polyvinylchloride (PVC), polyvinylidene chloride (PVDC), polyvinyl fluoride (PVF), acrylonitrile-acryloid-styrene (AAS), acrylonitrile-butadiene-styrene (ABS), and acrylonitrile-chlorizate ethylene-styrene (ACS), any other suitable polymers provided by Biogenera Advanced Fiber Technology (http://www.biogeneral.com/). Other materials useful for manufacturing the micro-containers are membraneous materials such as nylon, cellulose, nitrocellulose, glass, metal, and semi-conducting materials (e.g. silicon and germanium).

Whereas the subject cell-filled tubes must be divisible, segments of tubes may vary in size, shape, vertical thickness and volume. A preferred tube is a microtubing, having a cross-sectional area in the range of about 0.01 mm$^2$ to about 5 cm$^2$. Preferably, the cross-sectional area is in the range of about 0.01 mm$^2$ to about 0.5 cm$^2$, more preferably from about 0.1 mm$^2$ to about 5 mm$^2$, and even more preferably from about 0.1 mm$^2$ to about 0.5 mm$^2$. Although any length of microtubing can be employed in preparation for the cell arrays of the present invention, those with even concentricity and consistent diameter are preferred.

Cell packaging:

Preparation of the arrays of tubes generally proceeds with loading cells of selected types into the individual tubes of the array. Each tube thus encloses a population of a specific type of cells. The selection of cell types is determined largely by the intended purpose of the cell array. The amount of cells packed into a tube will typically depend on the number of cells per cross-sectional area that is required for the intended cell-based assays. To detect a cellular protein of average abundance by immunostaining, each section typically contains about $1\times10^5$ cells/cm$^2$ to about $5\times10^6$ cells/cm$^2$. Accordingly, for a microtubing having a cross-sectional area in the range of about 0.3 mm$^2$ to about 3 mm$^2$, cells are loaded at a density of about $10^6$ to $10^9$ cells/cm$^3$, preferably about $10^7$ to $4\times10^8$ cells/cm$^3$, and even more preferably about $3\times10^7$ to $2\times10^8$ cells/cm$^3$.

To immobilize cells in a tube, cells can be packed to form a dense pellet. Alternatively, cells can be loaded with a viscous substance such as an immobilizing matrix. A variety of matrixes are available in the art, which include agar, Methocell®, Matrix gel®, OCT compounds, paraffin, denatured and non-denatured collagen, fibronectin, laminin, and mixtures thereof. Those skilled in the art will know of other suitable matrixes for cell immobilization, or will be able to ascertain such, without undue experimentation.

In certain embodiments of the invention, the immobilizing matrix can be supplemented with nutrients or other components of a cell-culture medium in order to maintain cell viability. The general parameters governing prokaryotic and eukaryotic cell survival are well established in the art. Physicochemical parameters which may be controlled in vitro are, e.g., pH, $CO_2$, temperature, and osmolarity. The nutritional requirements of cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, most cells also require one or more hormones from at least one of the following groups: steroids, prostaglandins, growth factors, pituitary hormones, and peptide hormones to survive or proliferate (Sato, G. H., et al. in "Growth of Cells in Hormonally Defined Media", Cold Spring Harbor Press, N.Y., 1982; Ham and Wallace (1979) Meth. Enz., 58:44, Barnes and Sato (1980) Anal. Biochem., 102:255, or Mather, J. P. and Roberts, P. E. (1998) "Introduction to Cell and Tissue Culture", Plenum Press, New York. Given the vast wealth of information on the nutrient requirements, medium conditions optimized for cell survival, one skilled in the art can readily fashion arrays of tubes carrying desired cell types using any one of the aforementioned methods and compositions, alone or in any combination. Where desired, tubes filled with cells may be stored at low temperature (e.g. −80° C.) for later uses. To prevent cell damage during the "freeze-and-thaw" process, cryopreservative agent such as DMSO, glycerol or sucrose is generally added to the cells at an appropriate concentration.

Preparing tube arrays:

Prior to sectioning, loaded tubes may be grouped together in any convenient pattern so that transverse-sections of the bundle may form a grid, a circular, ellipsoid, oval or some other analogously curved shape. The tubes can be grouped in a configuration such that their relative positions serve to orient the array. The total number of tubes may vary depending on the number of unique cell types one wishes to display in the cell array, as well as the number of control cell types, as may be desired depending on the particular application in which the subject array is to be employed. Generally, the pattern present on the surface of the cell array comprises at least about 3 distinct cell types, usually at least about 10 distinct cell types, and more usually at least about 20 distinct cell types, where the number of cell types may be as high as 100 or higher, but usually does not exceed about 5,000 distinct cell types, and more usually does not exceed about 1,000 distinct cell types. In many embodiments, it is preferable to have each distinct cell composition presented in duplicate to quadruplicate, so that there are two to four tubes for each distinct cell type on the cell array. The individual tubes in an array can be distinguished and identified by their relative positions, their distinct colors, or detectable labels that are unique to each member of the array.

Preparation of the sections of arrayed tubes can be performed according to standard techniques of histochemistry. Briefly, the array of filled tubes is first embedded in a substance known as "embedding agent" that hardens to a firm, easily sectioned material. Commonly employed embedding agents include but are not limited to paraffin, nitrocellulose, glue, collagen (denatured or non-denatured), fibronectin, laminin, gum syrup, OCT compounds, and various formulations of plastic polymers. The embedding agent is allowed to solidify around and between each tube in an array. For paraffin embedding, dehydration of the tube arrays is generally required prior to embedment to remove excess water or moisture. Typically, dehydration is accomplished by immersing the array in increasing concentrations of dehydrating agent such as alcohol and the like. Traces of dehydrating agent are then removed by clearing agents immediately before embedment. Most commonly used clearing agents are benzene, chloroform, toluene, xylol, dioxane and mixtures of various oils.

Sectioning embedded tube arrays can be carried out using a variety of cutting instruments well known to artisans in the field. Representative instruments are standard microtome for cutting sections having a vertical thickness ranging from about 1 to 100 microns, ultramicrotome for sections thinner than 1 micron, and cryostat microtome for frozen sections. The vertical thickness (or length) of a tube segment is largely determined by the cellular phenotype that one chooses to investigate. Where the purpose is to discern the differential expression of a cell surface antigen, tube segments generally have a minimal vertical thickness (or length) of one cell layer. The average thickness of different types of cells may vary. For mammalian cells, segments of about 4 to 20 microns generally encompass at least one cell layer. When analyzing intracellular structures, thinner segments ranging from about 1 to about 4 micron are preferred. A skilled artisan can routinely modify the aforementioned parameters of sectioning, the procedures for dehydration and/or embedding based on a variety of well-established protocols for histological analyses (see Animal Tissue Techniques, G. L Humason (1967) W. H. Freeman & Company, and protocols posted at http://www.gac.edu/; http://www.ccc.nottingham.ac.uk/; http://www.hei.org/).

Upon completion of sectioning the tube arrays, tube segments are immobilized onto a solid support by any suitable techniques that effect in stable association of the segments with the surface of a solid support. Preferably, each segment immobilized on the solid support has an exposed upper cross-sectional surface. By stably associated is meant that the tube segments containing cells of desired type maintain their position relative to the solid support under subsequent cell-based analyses including but are not limited to hybridization and immunostaining. As such, the tube segments can be directed attached to the support surface via covalent or non-covalent bonds, or mechanically affixed onto the support (e.g. by the means of mounting). Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Covalent association involves formation of chemical bond between the cells or the material of the tube and a functional group present on the surface of a support. The functional group may naturally occurring or introduced as a linker. Non-limiting functional groups include but are not limited to hydroxyl, amine, thiol and amide. Exemplary techniques applicable for covalent immobilization of cells include, but are not limited to, UV cross-linking or other light-directed chemical coupling, and mechanically directed coupling (see, e.g. U.S. Pat. No. 5,324,591; Aplin et al. *Anlayti. Biochem* (1981) 113:144–148; Mrksich et al. Ann. Rev. Biophys. Biomol. Struct. (1996) 25:55–78). A preferred method is to mount the sections to a solid support using any suitable mounting agents (see e.g. description at pages 132–134 in Animal Tissue Techniques, G. L Humason (1967) W. H. Freeman & Company). Methods and compositions useful for mounting sliced sections are well established in the art, and hence are not detailed herein.

The solid support on which arrays of tubes are attached comprises at least one surface, which may be smooth or substantially planar, with irregularities such as depressions or elevations. The solid support may be substantially impermeable or sufficiently porous to allow access of reactants. In certain embodiments, the solid support is connected to a base chamber that supplies reactants or therapeutic agents to be tested in a cell-based assay. For instance, a network of microfluidic channels (see e.g. WO 97/45730) can be combined with the solid support to deliver reactants to each tube of cells immobilized thereon.

The substrates of the subject cell arrays may be manufactured from a variety of materials. In general, the materials with which the support is fabricated exhibit a low level of non-specific binding during hybridization or immunoassay. A preferred solid support is made from one or more of the following types of materials: plastic polymers, glass, cellulose, nitrocellulose, semi-conducting material, and metal. The materials may be flexible or rigid. A flexible substrate is capable of being bent, folded, twisted or similarly manipulated, without breaking. A rigid substrate is one that is stiff or inflexible and prone to breakage. As such, the rigid substrates of the subject arrays are sufficient to provide physical support and structure to the tubes present thereon under the assay conditions in which the arrays are employed, particularly under high throughput assay conditions. Exemplary materials suitable for fabricating flexible support include a diversity of membranous materials, such as nitrocellulose, nylon or derivatives thereof, and plastic polymers (e.g. polytetrafluoroethylene, polypropylene, polystyrene, polycarbonate, and blends thereof). Examples of materials suitable for making rigid support include but are not limited to glass, semi-conductors such as silicon and germanium, metals such as platinum and gold. In many situations, it will also be preferable to employ a solid support that is transparent to visible and/or UV light.

The surface on which the pattern of tubes is arrayed may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers coated on the solid support may comprise inorganic layers made of, e.g. metals, metal oxides, or organic layers composed of polymers or small organic molecules and the like. Polymeric layers of interest include layers of peptides, proteins, polysaccharides, lipids, phospholipids, polyurethanes, polyesters, polycarbonates, polyureas, polyamides, polyethyleneamines, polyarylene sulfates, polysiloxanes, polyimides, polyacetates and the like, where the polymers may be hetero- or homopolymeric, and may or may not be conjugated to functional moieties. A preferred modification is to coat a glass slide with a layer of aminosilane such as 3-aminopropyltriethoxysilane (APTS).

The solid supports upon which the subject cell arrays are presented may take a variety of configurations ranging from simple to complex, depending on the intended use of the array. Thus, the substrate could have an overall slide or plate configuration, such as a rectangular or disc configuration. In many embodiments, the substrate may have a rectangular cross-sectional shape, having a length in the range of about 10 mm to 100 cm, usually about 0.1 cm to 10 cm and more usually about 1 cm to 5 cm; and a width in the range of about 10 mm to 100 cm, usually about 0.1 cm to 10 cm, and more usually about 1 cm to 5 cm; and a thickness in the range of about 0.001 mm to 5 cm, usually about 0.01 mm to 1 cm, and more usually about 0.1 mm to 2 mm.

Uses of the Cell Arrays of the Present Invention

The subject cell arrays provide an effective means for simultaneous detection of the expression of a target polynucleotide or protein in a multiplicity of cell types. The expression detecting methods may be used in a wide variety of circumstances including identification and quantification of differential gene expression between diseased and normal tissues, among different types of tissues and cells, amongst cells at different developmental stages or at different cell-cycle points, and amongst cells that are subjected to various environmental stimuli or lead drugs. As such, the subject arrays have a broad spectrum of utility in, e.g. drug screening, disease diagnosis, phylogenetic classification, parental and forensic identification.

Simultaneous detection of a target polynucleotide in multiple cell types:

In one embodiment, this invention provides a method of detecting differential expression of a target polynucleotide in a multiplicity of cell types. The method comprises the steps of: (a) providing an array of immobilized tubes of the subject invention, wherein each tube has a lumen and a population of cells that is contained and immobilized within said lurnen, and polynucleotides of the cells contained in at least one of the tubes of the array are denatured; (b) contacting a nucleotide probe corresponding to the target polynucleotide with the array under conditions sufficient to produce a stable probe-target complex; and (c) detecting the formation of the stable probe-target complex in each tube of the array that forms a hybridization pattern representative of the differential expression of said polynucleotide in the multiplicity of cell types.

In another embodiment, the invention provides a method for detecting differential expression of a target polynucleotide in multiple cell types derived from at least two subjects. The method involves the steps of: (a) hybridizing a first cell array of claim 16 with a nucleotide probe corresponding to the target polynucleotide under conditions sufficient to produce a stable probe-target complex, wherein the array comprises a plurality of tubes containing a multiplicity of cell types of a first subject; (b) detecting the formation of the probe-target complex in each tube of the array that forms a hybridization pattern representative of the differential expression of said polynucleotide in the multiplicity of cell types of the first subject; (c) hybridizing a second cell array of claim 16 with a nucleotide probe corresponding to the target polynucleotide under conditions sufficient to produce a stable probe-target complex, wherein the array comprises a plurality of tubes containing a multiplicity of cell types of a second subject; (d) detecting the formation of the probe-target complex in each tube of the array that forms a hybridization pattern representative of the differential expression of said polynucleotide in the multiplicity of cell types of the second subject; and (e) comparing the hybridization patterns, thereby detecting differential expression of a target polynucleotide in a multiplicity of cell types of the subjects.

As used herein, nucleotide probes "corresponding to" a target polynucleotide expressed in a test cell, refer to the nucleic acids whose entire sequences or contiguous fragments thereof share substantial sequence homology to that of the target polynucleotide. In general, substantially homologous sequences share at least about 80% nucleotide base identity when optimally aligned, preferably about 90% identity, more preferably about 95% identity. Sequence homology can be ascertained with the aid of computer programs. Exemplary homology search programs include Blast (see http://www.ncbi.nlm.nih.gov/blast/), Fasta (Computing Group package, Madison, Wis., USA), DNA Star, MegAlign, and GeneJocky.

In designing nucleotide probes for detecting a specific sequence in whole cell mounts, it is preferable to select probes which are specific to the target sequence, and unique to the entire genome of the test cells. Such unique probe lacks substantial sequence homology with any other endogenous genes when optimally aligned, and thus having a low probability of cross-hybridizing with other genes present in the test cells. Secondly, preferred nucleotide probes exhibit minimal secondary structures and internal sequence homology. Extensive homology within the probe due to e.g., inverted repeats, promotes self-hybridization, and thus interfering the binding of the probe to the target sequences. Nucleotide probes employed in the in situ hybridization generally have a minimal length about 10 nucleotides, more preferably about 50 nucleotides, and even more preferably about 100 nucleotides. Preferably, probes have a maximum length about 10,000 nucleotides, more preferably about 5000 nucleotides, more preferably 1000 nucleotides, and even more preferably about 500 nucleotides. Both RNA and DNA molecules can be employed as probes for an in situ detection of a target sequence.

Preparation of the nucleotide probes can be carried out by chemical synthesis, recombinant cloning, e.g. PCR, or any combination thereof. Methods of chemical polynucleotide synthesis and recombinant techniques for generating desired nucleotide sequences are known to those of skill in the art and need not be described in detail herein.

Prior to hybridization, the array of cells are typically pretreated to: (a) preserve the cell morphology (fixation); (b) inactivate cellular enzymes that may interfere with hybridization or detection of the target sequence; (c) permeablize and extract the lipid membrane to enhance target accessibility (detergent and/or proteinase treatment); and (d) denature the target polynucleotides (if double stranded) to effect hybridization with selected probes. Procedures for each pretreament listed above are well established in the art (see e.g. Nonradioative In Situ Hybridization Application Manual, Boehringer Mannheim, second edition), and thus are not detailed herein.

In assaying for the presence of target polynucleotides in multiple cell types, probes are allowed to form stable complexes with the target polynucleotides contained within cells affixed on the aforementioned arrays in a hybridization reaction. It will be appreciated by one of skill in the art that where antisense is used as the probe nucleic acid, the target polynucleotides provided in the array are chosen to be complementary to sequences of the antisense nucleic acids. Conversely, where the nucleotide probe is a sense nucleic acid, the target polynucleotide is selected to be complementary to sequences of the sense nucleic acid.

Suitable hybridization conditions for the practice of the present invention are such that the recognition interaction between the probe and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra; Nonradioative In Situ Hybridization Application Manual, Boehringer Mannheim, second edition).

In general, there is a tradeoff between hybridization specificity (stringency) and signal intensity. In a preferred embodiment, washing the hybridized array prior to detecting the target-probe complexes is performed to enhance the noise-signal ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

For a convenient detection of the probe-target complexes formed during the hybridization assay, the nucleotide probes are conjugated to a detectable label. Detectable labels suitable for use in the present invention include any composition detectable by spectroscopic, photochemical, biochemical, immunochemical, electrical, optical or chemical means. A wide variety of appropriate detectable labels are known in the art, which include luminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The labels may be incorporated by any of a number of means well known to those of skill in the art. In one aspect, the label is simultaneously incorporated during the amplification step in the preparation of the nucleotide probes. Thus, for example, polymerase chain reaction (PCR) with labeled primers or labeled nucleotides can provide a labeled amplification product. In a separate aspect, transcription reaction, as described above, using a labeled nucleotide (e.g. fluorescein-labeled UTP and/or CTP, digoxigenin-UTP) or a labeled primer, incorporates a detectable label into the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

The detection methods used to determine where hybridization has taken place and/or to quantify the hybridization intensity will typically depend upon the label selected above. For example, radiolabels may be detected using photographic film or phosphoimager (for detecting and quantifying $^{32}P$ incorporation). Fluorescent markers may be detected and quantified using a photodetector to detect emitted light (see U.S. Pat. No. 5,143,854 for an exemplary apparatus). Enzymatic labels are typically detected by providing the enzyme with a substrate and measuring the reaction product produced by the action of the enzyme on the substrate; and finally colorimetric labels are detected by simply visualizing the colored label.

One of skill in the art, however, will appreciate that hybridization signals will vary in strength with efficiency of hybridization, the amount of label on the target nucleic acid and the amount of particular target nucleic acid in the sample. In evaluating the hybridization data, a threshold intensity value may be selected below which a signal is not counted as being essentially indistinguishable from background. In addition, the provision of appropriate controls permits a more detailed analysis that controls for variations in hybridization conditions, cell health, non-specific binding and the like.

The detection method provides a positional localization of the tube where hybridization has taken place. The position of the hybridized region correlates to the specific cell type in which the target polynucleotide is present in a detectable amount. The detection methods also yield quantitative measurement of the level of hybridization intensity at each hybridized region, and thus a direct measurement of the abundance, or expression level of a given sequence. A collection of the data indicating the regions of hybridization present on an array and their respective intensities constitutes a "hybridization pattern" that is representative of the expression profile of the target sequence in a multiplicity of cell types derived from a subject. Any discrepancies detected in the hybridization patterns generated by hybridizing cells from different subjects are indicative of differential representation of a target polynucleotide in a multiplicity of cell types of these subjects.

In one aspect, the hybridization patterns to be compared can be generated on the same array. In such case, different patterns are distinguished by the distinct types of detectable labels or by using multiple sections of the array, each being incubated with a different nucleotide probe. In a separate aspect, the hybridization patterns employed for the comparison are generated on different arrays, where discrepancies are indicative of a differential expression of a particular gene in the subjects being compared.

Simultaneous detection of a target protein in multiple cell types:

In a separate embodiment, the present invention provides a method of simultaneously detecting the presence of a specific protein-protein interaction involving a proteinaceous probe and a target protein in multiple types of cells. The method involves the steps: (a) providing a cell array comprising multiple types of cells contained in tubes that are immobilized on a solid support; (b) contacting a proteinaceous probe that is specific for a target protein with the array of tubes under conditions sufficient to produce stable probe-target complex; and (c) detecting the formation of the stable probe-target complex in each tube, thereby detecting the presence of specific protein-protein interaction in multiple types of cells.

In one aspect of this embodiment, the protein-protein interaction is between a target protein (i.e. an antigen) and an antibody specific for that target. In another aspect, the protein-protein interaction is between a cell surface receptor and its corresponding ligand. In yet another aspect, the protein-protein interaction involves a cell surface receptor and an immunoliposome or an immunotoxin; in other aspects, the protein-protein interaction may involve a cytosolic protein, a nuclear protein, a chaperon protein, or proteins anchored on other intracellular membranous structures. The methods are useful for discerning or confirming the differential expression of a target protein in multiple cell types of interest using a proteinaceous probe, selected from the group consisting of an antibody, a receptor ligand, a secreted protein, cell surface receptor, cytosolic protein, nuclear protein, immunoliposome, and immunotoxin. The detection methods may also be employed to measure the kinetics of the protein-protein interaction in question. Kinetic measurements encompass but are not limited to antibody binding affinities, ligand binding affinities, immunoliposome or immuotoxin uptake rate, and the rates of formation and dissociation of a protein-protein complex.

The reaction is performed by contacting the proteinaceous probe with a cell array of particular interest under conditions that will allow a complex to form between the probe and the target. The formation of the complex can be detected directly or indirectly according standard procedures in the art. In the direct detection method, the probes are supplied with a detectable label and unreacted probes may be removed from the complex; the amount of remaining label thereby indicating the amount of complex formed. For such method, it is preferable to select labels that remain attached to the probes even during stringent washing conditions. It is more important, however, that the label does not interfere with the binding reaction. In the alternative, an indirect detection procedure requires the probe to contain a label introduced either chemically or enzymatically, that can be detected by affinity cytochemistry. A desirable label generally does not interfere with target binding or the stability of the resulting target-probe complex. However, the label is typically designed to be accessible to an antibody for an effective binding and hence generating a detectable signal. A wide variety of labels are known in the art. Non-limiting examples of the types of labels which can be used in the present invention include radioisotopes, enzymes, colloidal metals, fluorescent compounds, bioluminescent compounds, and chemiluminescent compounds.

The amount of probe-target complexes formed during the binding reaction can be quantified by standard quantitative assays. As illustrated above, the formation of probe-target complex can be measured directly by the amount of label remained at the site of binding. In an alternative, the target protein is tested for its ability to compete with a labeled analog for binding sites on the specific probe. In this competitive assay, the amount of label captured is inversely proportional to the amount of target protein present in a test cell population.

One important application of the in situ analysis using the subject cell array is the determination of tissue and/or intracellular localization of a target protein of particular interest. Distinguished from traditional approaches in which sections of frozen or fixed tissues and cells of a specific type were examined one at a time, the subject method permits simultaneous detection of the target protein on a miniaturized array of multiple cell types, and hence greatly simplifies the conventional procedures.

In assaying a tissue array for the differential expression of a target protein, it is preferable to include a control probe known to react with the selected cells. When analyzing the intracellular localization of a target protein, standard cytoimmunostaining techniques known to skilled artisans can be employed. Cytoimmunostaining may be performed directly on frozen sections of cells or tissues or, preceded by fixing cells with a fixative that preserves the intracellular structures, followed by permeablization of the cell to ensure free access of the probes. The step of permeablization can be omitted when examining cell-surface antigens. After incubating the cell preparations with a probe such as an antibody specific for the target, unbound antibody is removed by washing, and the bound antibody is detected either directly (if the primary antibody is labeled) or, more commonly, indirectly visualized using a labeled secondary antibody. In localizing a target polypeptide to a specific subcellular structure in a cell, co-staining with one or more marker antibodies specific for antigens differentially present in such structure is preferably performed. A battery of organelle specific antibodies is available in the art. Non-limiting examples include plasma membrane specific antibodies reactive with cell surface receptor Her2, endoplasmic reticulum (ER) specific antibodies directed to the ER resident protein Bip, Gogli specific antibody α-adaptin, and cytokeratin specific antibodies which will differentiate cytokeratins from different cell types (e.g. between epithelial and stromal cells) or in different species. To detect and quantify the immunospecific binding, digital image analysis system coupled to conventional or confocal microscopy can be employed.

Of particular interest are the target proteins exhibiting restricted tissue, cell-type or subcelluar distribution patterns. Within this category, the cellular targets with major diagnostic and/or therapeutic potential are those selectively expressed in a disease tissue or disease cell type. In recent years, numerous cancer cell marker proteins have been identified through screening a wide spectrum of normal and cancerous tissues and cell types. A well-characterized breast cancer cell surface marker, Her2 receptor, is found to be expressed at an abnormally high level in a subset of the breast cancer tissue and not in normal tissues. A humanized anti-Her2 antibody, available commercially and in the trademark Herceptin®, which selectively binds to breast cancer cells, has been developed and used as a potent drug to treat tens and thousands of breast cancer patients over-expressing Her2 receptors. Thus, the miniaturized cell arrays of the subject invention immobilized with a vast variety of cell types find utility in the selection of antibodies exhibiting desired cell-type binding selectively. Accordingly, the present invention encompasses a method for determining the cell-type binding selectivity of an antibody using the subject cell arrays.

The target protein detection method provides a positional localization of the tube where protein-protein interaction has taken place. The position of the tube where interaction takes place correlates to the specific cell type in which the target protein is present in a detectable amount. The detection methods also yield quantitative measurement of the level of interaction (e.g. intensities of immunostain) within each tube, and thus a direct measurement of the abundance, or expression level of a given protein. A collection of the data indicating the regions of protein-protein interaction on a cell array and their respective intensities constitutes, e.g. an "immunostaining pattern" that is representative of the expression profile of the target protein in a multiplicity of cell types derived from a subject. Any discrepancies detected in the immunostaining patterns observed in different subjects are indicative of differential representation of a target polypeptide in a multiplicity of cell types of these subjects.

In one aspect, the immunostaining patterns to be compared can be generated on the same array either by using different probes to simultaneously detect different proteins on the same section of the same array or by using multiple sections of the same array, each being incubated with a different probe. In such case, different patterns are distinguished by the distinct types of detectable labels. In a separate aspect, the immunostaining patterns employed for the comparison are generated on different arrays, where discrepancies are indicative of a differential expression of a particular target protein in the subjects being compared.

The arrays employed for the comparative in situ analyses (including hybridization, immunoassay, or a combination thereof) may be embryonic cell arrays, adult cell arrays, primary cell arrays, cell line arrays, tissue arrays, mammalian cell arrays, zoo arrays, genetically altered cell arrays, chemically treated cell arrays, or disease cell arrays. Comparative analyses conducted on this vast arrays of cell types greatly facilitate the identification of genes and gene products of a specific developmental origin, such as those expressed in embryo or an adult, during ectoderm, endoderm or mesoderm formation in a multi-cellular organism. Such analyses can also aid in the detection of distinct classes of genes and polypeptides that play a pivotal role in the development of a specific tissue, or contribute to a particular disease phenotype. Furthermore, the comparative analyses allow effective screening for compounds capable of modulating a signal transduction pathway, which would be of major diagnostic and/or therapeutic potential.

Identification of modulators of a signal transduction pathway:

The activity of cells is regulated by external signals that stimulate or inhibit intracellular events. The process by which stimulatory or inhibitory signals are transmitted into and within a cell to elicit an intracellular response is referred to as signal transduction. Proper signal transduction is essential for proper cellular function. Over the past decades, numerous cellular signaling molecules have been identified, cloned and characterized. Non-limiting examples of the signaling proteins include cell surface receptors, protein kinases (e.g. tyrosine, serine/threonine or histidine kinases), trimeric G-proteins, cytokines, SH2-, SH3-, PH-, PDZ-, death-domain containing proteins, and any of those gene or protein families published by Human Genome Sciences Inc., Celera, the Institute for Genomic Research (TIGR), and Incyte Pharmaceuticals, Inc. Cascades of signal transduction events mediated by the ever-growing families of signaling proteins have been elucidated and found to play a central role in a variety of biological responses. Among them are cell cycle regulation, cell differentiation, apoptosis, chemotaxis, cell motility and cytoskeletal rearrangement (Cantley et al. (1991) *Cell* 64:281–302); Liscovitch et al. (1994) *Cell* 77:329–334). Defects in various components of signal transduction pathways have also been found to account for a vast number of diseases, including numerous forms of cancer, vascular diseases and neuronal diseases. Indeed, modulators of signaling pathways have long been acknowledged as potential diagnostic and/or therapeutic agents.

Accordingly, the present invention provides a method for identifying a modulator of a signal transduction pathway. The method involves the following steps: (a) providing a subject cell array, wherein at least a subset of tubes contains cells expressing at least one reporter molecule that yields a detectable signal transduction readout; (b) contacting the array with a candidate modulator; and (c) assaying for a change in the signal transduction readout, thereby identifying a modulator of the signal transduction pathway.

The choice of reporter molecule is dependent on the signal transduction pathway that is under investigation. For example, when examining a signaling cascade involving a fluctuation of intracellular pH condition, pH sensitive molecules such as fluorescent pH dyes can be used as the reporter molecules. In another example where the signaling pathway of a trimeric $G_q$ protein is analyzed, calcium-sensitive fluorescent probes can be employed as reporters. As is apparent to artisans in the field of signal transduction, trimeric $G_q$ protein is involved in a classic signaling pathway, in which activation of $G_q$ stimulates hydrolysis of phosphoinositides by phospholipase C to generate two classes of well-characterized second messengers, namely, diacylglycerol and inositol phosphates. The latter stimulates the mobilization of calcium from intracellular stores, and thus resulting in a transient surge of intracellular calcium concentration, which is a readout measurable with a calcium-sensitive probe.

Another exemplary class of reporter molecules is a reporter gene operably linked to an inducible promoter that can be activated upon the stimulation or inhibition of a signaling pathway. Reporter proteins can also be linked with other proteins whose expression is dependent upon the stimulation or suppression of a given signaling cascade. Commonly employed reporter proteins can be easily detected by a colorimetric or fluorescent assay. Non-limiting examples of such reporter proteins include: β-galactosidase, β-lactamase, chloramphenicol acetyltransferase (CAT), luciferase, green fluorescent protein (GFP) and their derivatives. Those skilled in the art will know of other suitable reporter molecules for assaying changes in a specific signaling transduction readout, or will be able to ascertain such, using routine experimentation.

To practice the screening method, a selected cell array is first exposed to candidate modulators. Where the modulator is a composition other than naked DNA or RNA, the modulator may be directly added to the tubes of cells immobilized on a solid support. As is apparent to those skilled in the art, an "effective" amount must be added which can be empirically determined. When the modulator is a polynucleotide, it may be introduced directly into a cell by transfection or electroporation. Alternatively, it may be inserted into the cell using a gene delivery vehicle or other methods known in the art.

For the purposes of this invention, a "modulator" is intended to include, but not be limited to a biological or chemical compound such as a simple or complex organic or inorganic molecule, a peptide, a protein (e.g. antibody) or a polynucleotide (e.g. anti-sense). A vast array of compounds can be synthesized, for example polymers, such as polypeptides and polynucleotides, and synthetic organic compounds based on various core structures, and these are also included in the term "modulator". In addition, various natural sources can provide compounds for screening, such as plant or animal extracts, and the like. It should be understood, although not always explicitly stated that the modulator is used alone or in combination with another modulator, having the same or different biological activity as the modulators identified by the inventive screen.

All types of cell arrays embodied by the present invention can be employed in a screen of candidate modulators. A preferred cell array containing cells carrying reporter molecules. A more preferred cell array contains living cells immobilized on a permeable solid support that permits access of modulators. Even more preferably, the solid support is attached to an array of microfluidic channels that supplies an array of modulators of the same kind or distinct types to the multiple cell types being tested. Such setup allows real-time recordation and analysis of cellular activities in response to candidate modulators.

The detection and/or quantification of change in the signal transduction readout will typically depend upon the reporter molecules selected above. Enzymatic reporter molecules are typically detected by providing the enzyme with a substrate and measuring the reaction product produced by the action of the enzyme on the substrate which gives rise a visible signal. For luminescent reporters, a variety of optical systems capable of detecting emitted light can be used. Exemplary setups include but are not limited to FLIPR™ (Molecular Devices, Inc.) which uses low angle laser scanning illumination and a mask to selectively excite fluorescence molecules; SAIC (Science Applications International Corporation) that employs a charged-coupled optical detector to image a whole cell array; and ArrayScan™ System (Cellomics, Inc., described in U.S. application Ser. No. 08/810983 and WO 98/38490) that can determine the distribution and activity of luminescent reporter molecules.

Computer Systems of the Present Invention

The determination of differential expression of a target polypeptide or protein in a multiplicity of cell types can be easily performed utilizing a computer. Accordingly, the present invention provides a computer-based system designed to detect differential expression of a target polynucleotide in multiple cell types derived from at least two subjects. Such system comprises:

A computer-based system for detecting differential expression of a target polynucleotide in a multiplicity of cell types derived from at least two subjects, wherein the differential representation is indicated by a difference in hybridization patterns on a cell array, the system comprising:

a) a data storage device comprising a reference hybridization pattern and a test hybridization pattern, wherein the reference hybridization pattern is generated by hybridizing a labeled nucleotide probe corresponding to the target polynucleotide to a cell array of claim 16, said array comprising a plurality of tubes containing a multiplicity of cell types of a reference subject; and wherein the test hybridization pattern is generated by hybridizing a labeled nucleotide probe corresponding to the target polynucleotide to a cell array of claim 16, said array comprising a plurality of tubes containing a multiplicity of cell types of a test subject; b) a search device for comparing the test hybridization pattern to the reference hybridization pattern of the data storage device of step (a) to detect the differences in hybridization patterns; and c) a retrieval device for obtaining said differences in hybridization patterns of step (b).

The present invention also provides a computer-based system for detecting differential expression of a target protein in a multiplicity of cell types derived from at least two subjects, based on differences in immunostaining patterns on a cell array of tubes. The system comprises: a) a data storage device comprising a reference immunostaining pattern and a test immunostaining pattern, wherein the reference immunostaining pattern is generated by staining a cell array of claim 16 with a labeled antibody that is specific for the target protein, said array comprising a plurality of tubes containing a multiplicity of cell types of a reference subject; and wherein the test immunostaining pattern is generated by staining a cell array of claim 16 with a labeled antibody that is specific for the target protein, said array comprising a plurality of tubes containing a multiplicity of cell types of a test subject; b) a search device for comparing the test immunostaining pattern to the reference immunostaining pattern of the data storage device of step (a) to detect the differences in immunostaining patterns; and c) a retrieval device for obtaining said differences in immunostaining patterns of step (b).

Generally a computer-based system includes hardware and software. The "data storage device" as part of the system refers to memory which can store reference and test hybridization or inununostaining pattern(s) generated by in situ hybridization or cytoimmunostaining using the subject arrays. The data-storage device may also include a memory access device which can access manufactures having recorded thereon the array information of the present invention. The term "recorded" refers to a process for storing information on computer readable medium. A skilled artisan can readily adopt any of the presently know methods for recording information on computer readable medium to generate manufactures comprising the arrays of the present invention. Non-limiting exemplary data storage devices are media storage, floppy drive, super floppy, tape drive, zip drive, syquest syjet drive, hard drive, CD Rom recordable (R), CD Rom rewritable (RW), M.D. drives, optical media, and punch cards/tape.

The "search device" as part of the computer-based system encompasses one or more programs which are implemented on the system to compare the test hybridization pattern to the reference hybridization pattern in order to detect the differences in these hybridization or immunostaining patterns. A variety of known algorithms are disclosed publicly and a variety of commercially available software useful for pattern recognition can be used in computer-based systems of the present invention. Examples of array analysis software include Biodiscovery, HP, and any of those applicable for image analyses. Some currently employed search devices include those embodied in "ArrayScan™ (Cellomics, Inc).

Finally, the retrieval device includes program(s) which are implemented on the system to retrieve the differences in hybridization or immunostaining patterns detected by the search device. Hardware necessary for displaying the detected device may also form part of the retrieval device. The storage, search, retrieval devices may be assemble as a PC, Mac, Apollo workstation (Cray), SGI machine, Sun machine, UNIX or LINUX based Workstations, Be OS systems, laptop computer, palmtop computer, and palm pilot system, or the like.

Further provided by the present invention is a computer-implemented method for determining differential expression of a target protein in a multiplicity of cell types, wherein the differential expression is indicated by differences in immunostaining patterns. The computer-implemented method comprises the following steps: (a) providing a database comprising immunostaining patterns that represent expression patterns of the target protein in multiplicity of cell types, wherein each immunostaining pattern is generated by staining a cell array of claim 16 with a labeled antibody that is specific for the target, wherein said staining step yields detectable antibody-target complexes with different levels of staining intensities; (b) receiving two or more immunostaining patterns for comparison; (c) determining differences in the selected immunostaining patterns; and (d) displaying the results of said determination.

Also embodied in the present invention is a computer-implemented method for detecting differential expression of a target polynucleotide in a multiplicity of cell types, based on differences in hybridization patterns. The computer-implemented method comprises the steps of: (a) providing a database comprising hybridization patterns that represent expression patterns of the polynucleotide in multiplicity of cell types, wherein each hybridization pattern is generated by hybridizing a cell array of claim 16 with a labeled nucleotide probe that is specific for the polynucleotide, wherein said hybridization step yields detectable target-probe complexes with different levels of hybridization intensities; (b) receiving two or more hybridization patterns for comparison; (c) determining differences in the selected hybridization patterns; and (d) displaying the results of said determination.

Kits Comprising the Cell Arrays of the Present Invention

The present invention also encompasses kits containing the cell arrays of this invention. Kits embodied by this invention include those that allow simultaneous detection of the expression and/or quantification of the level of expression of a target polynucleotide or protein in multiple cell types presented on a cell array.

Each kit necessarily comprises the reagents which render the in situ hybridization or immunostaining procedure possible: a cell array immobilized with multiple tube segments corresponding to a plurality of cell types to effect an in situ analyses; nucleotide probes useful for detecting target polynucleotides; proteinaceous probes applicable for detecting the target proteins; reagents that allow formation and detection of stable target-probe complexes during a hybridization reaction or a protein-protein binding assay. The kits may also contain reagents useful for generating labeled probes. Optionally, the arrays contained in the kits may be pre-hybridized with polynucleotides or stained with antibodies corresponding to genes and protein products the control to which the test subject is compare.

Each reagent can be supplied in a solid form or dissolved/suspended in a liquid buffer suitable for inventory storage, and later for exchange or addition into the reaction medium when the test is performed. Suitable individual packaging is normally provided. The kit can optionally provide additional components that are useful in the procedure. These optional components include, but are not limited to, buffers, capture reagents, developing reagents, labels, reacting surfaces, means for detection, control samples, instructions, and interpretive information. Diagnostic or prognostic procedures using the kits of this invention can be performed by clinical laboratories, experimental laboratories, practitioners, or private individuals.

Further illustration of the development and use of arrays and assays according to this invention are provided in the Example section below. The examples are provided as a guide to a practitioner of ordinary skill in the art, and are not meant to be limiting in any way.

EXAMPLES

Example 1

Immunostaining a Target Protein Using a Cell Array of the Present Invention

Standard cytoimmunostaining procedures were employed to detect two cellular protein targets, cytokeratin and vimentin, using a subject cell array. Cytokeratin is a cytoskeleton protein expressed only in human tumor epithelial cells, and vimentin is another cytoskeleton protein expressed primarily in non-epithelial cells. The array employed in this study contains multiple tubes of cells immobilized on a glass slide. Each tube comprises cells of a unique type selected from the group consisting of monkey (COS), hamster (CHO), primary human cell line (Schwann cells), human tumor cell lines Colo205, hCT1165, BT474, LNcap, and PC3.

Cells on the array were first fixed with ethanol (−20° C.), and air-dried for about 30 minutes. Alternative fixatives include but are not limited to formaldehyde, paraformaldehyde. To reduce the background staining signal, the cells were first incubated in a blocking solution (e.g. non-fat milk or 1–5% BSA in PBS buffer), and then in the buffer (PBS with 5% serum and 0.1% triton X-100) for one hour at room temperature.

An appropriate amount of primary antibodies specific for either cytokeratin or vimentin were added to the blocking buffer and allowed to bind to the cells on the array at about 37° C. for approximately 2 hours, or at 4° C. overnight. Unbound primary antibodies were removed by washing the cell array for approximately 3 times. The cell array was then immersed in a blocking solution containing secondary antibodies conjugated with an enzyme or a luminescent label for approximately 1 hour. Unbound secondary antibodies were washed away with milli-Q water. The detection of the secondary antibodies would depend on the type of labels conjugated to the secondary antibodies. For example, to visualize peroxidase-linked secondary antibodies, enzyme substrate comprising $DAB/H_2O_2$ in sodium acetate buffer, pH 5.0 can be used. To detect specific binding of alkaline phosphatase-linked secondary antibodies, Fastred/Texas Red dissolved in milli-Q water can be employed. The enzymatic reaction can be terminated by washing the unreacted substrates away using any suitable buffer.

Figure 2:
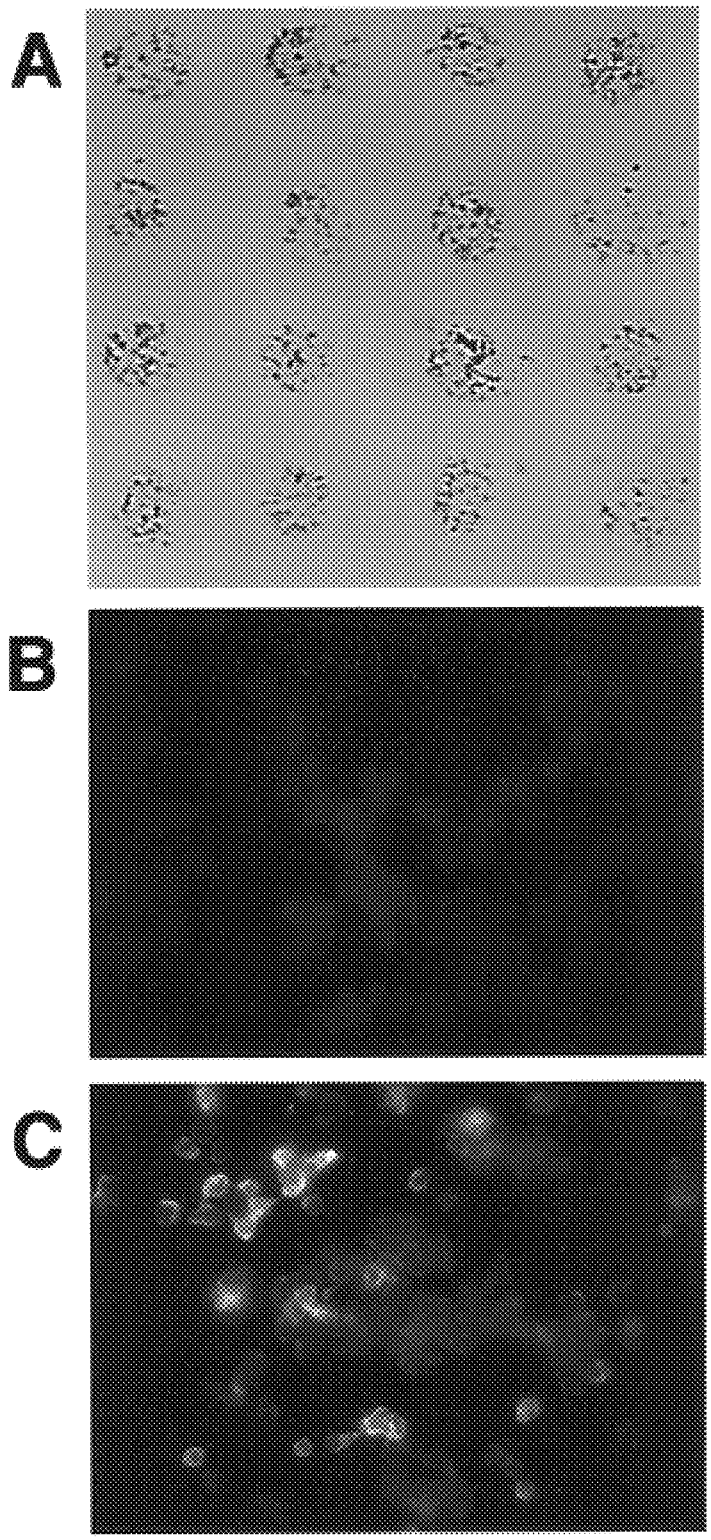
FIG. 2A is a top view (10× magnification) of a cell array stained with anti-hematoxylin antibodies reactive with a ubiquitously expressed protein, hematoxylin. Immobilized on the array are tubes of cells of unique types. Shown in the first row from left to right are Colo205 (human epithelial cell line), hCT1165, BT474, and LNcap cells. Second row displaces from the left PC3, COS, CHO, and primary human Schwann cell line. Cells shown in the third and the forth rows are replicates of those displaced in the first and second rows, respectively.
FIG. 2C represents an anti-cytokeratin stain of a single tube of human prostate carcinoma LNcap epithelial cells.
FIG. 2B is a reproduction of the anti-vimentin stain of the same tube of cells in the cell array, which serves as a negative control.

A specific stain of cytokeratin was detected in the above-listed human epithelial tumor cells but not in CHO, COS, and Schwann cells. By contrast, a specific stain of vimentin was only detected in CHO, COS, and Schwann cells and not in the human epithelial tumor cells (Table 1, FIG. 2B and 2C). These results demonstrate the applicability of the subject array in detecting differential expression of target proteins.

TABLE 1

Immunocytochemical staining a subject cell array with anti-cytokeratin and anti-vimentin antibodies

| | Colo-205 | HCT 1165 | BT 474 | LNcap | PC3 | COS | CHO | human Schwann Cells |
|---|---|---|---|---|---|---|---|---|
| Cytokeratin | + | + | + | + | + | − | − | − |
| Vimentin | − | − | − | − | − | + | + | + |

"+" indicates that target protein was detected in the cells selected; and "−" indicates that the target protein was undetectable in the selected cells in an immunostaining assay.

Example 2

Preparation of Cryosections

An array of tubes loaded with cells of particular interest was first placed in a mold. The mold was then filled with OCT compound to effect cutting and handling of frozen sections. The mold was then placed on an isopropanol/dry ice bath to freeze the cells immobilized inside the array of tubes. The tube array may be stored at low temperature (e.g. −80° C.) and sectioned when needed.

Sectioning the frozen tube array can be carried out using a cryostat microtome as follows. The frozen tube array was first placed inside the cryostat for equilibration for about 30 minutes. The mold was then removed, and the tube array was put on the aligning chips with OCT compound. Upon alignment of the chips, the tube array was sectioned to yield segments of tubes of defined thickness or length. The segments were then thawed for subsequent immobilization onto a selected solid support. Typically, the segments were mounted onto a glass slide or cover slip. Generally, the tube segments were allowed to dry at room temperature for about 15 to about 30 minutes to effect stable attachment to the solid support. The resulting cell array again may be stored at low temperature (e.g. −70° C.) for later uses.

Example 3

Immunofluorescence Study of Cryosections

A cell array prepared by cryosectioning a tube array comprises a plurality of frozen and unfixed cell populations. Procedures for immunofluorescence study with unfixed cells are well established in the art. Typically, the process proceeds with placing the cell array in a humid chamber (e.g. 150 mm dishes). The cells on the array were then incubated in a blocking buffer containing proteinase inhibitors to prevent enzymatic degradation of the primary and secondary antibodies by endogenous proteinases. A typical blocking buffer is made of 5% BSA or normal serum from the species of the secondary antibody that will be used, 1 mM PMSF, 10 μg/ml aprotinin, and 1 μg/ml leupeptin, 0.1% Tween 20 in PBS solution. Upon incubation with an appropriate amount of primary antibodies, the cells were then fixed with ethyl alcohol at −20° C. Fixation carried out subsequent to the binding of primary antibodies avoids alterations of antigen binding sites, if any, by the fixative. Such procedure is also applicable for assaying for ligand-receptor binding. The primary antibodies may then be visualized using conjugated secondary antibodies as stated in Example 1.

We claim:

1. A cell array comprising a plurality of tube segments obtained by cross-sectioning a tube array containing frozen viable cells, wherein each tube segment of the cell array has at least one lumen and a population of frozen viable cells of a specific type that is contained and immobilized within said lumen.

2. The cell array of claim 1, wherein each tube segment of the array is immobilized on a solid support.

3. The cell array of claim 2, wherein at least a subset of said plurality comprises at least two tube segments, each tube segment of the subset containing cells of a unique type.

4. The cell array of claim 2, wherein the population of cells is embedded in a matrix.

5. The cell array of claim 2, wherein at least one tube segment in the array has more than one lumen.

6. The cell array of claim 2, wherein each tube segment of the array is made of plastic polymer, glass, cellulose, nitrocellulose, semi-conducting material, metal, or any combination thereof.

7. The cell array of claim 2, wherein each tube segment contains at least 10 cells of the same type.

8. The cell array of claim 2, wherein each tube segment contains at least 100 cells of the same type.

9. The cell array of claim 2, wherein at least one of the tube segments contain control cells.

10. The cell array of claim 2, wherein the solid support is made of plastic polymer, glass, cellulose, nitrocellulose, semi-conducting material, metal, or any combination thereof.

11. The cell array of claim 3, wherein at least one tube segment in the subset has multiple lumens, wherein each lumen of said at least tube segment contains a cell population that is unique with respect to all other cell populations contained in other lumens of the tube segments of the subset.

12. The cell array of claim 3, wherein at least one tube segment in the subset has multiple lumens, wherein each lumen of said at least one tube segment contains a cell population that is unique with respect to all other cell populations contained in other lumens of the same tube segment.

13. The cell array of claim 3, wherein cells contained in the different tube segments of the subset differ in one or more of the characteristics selected from the group consisting of genotypic characteristics, species, origin, developmental stage, developmental origin, tissue origin, chemical treatment, cell-cycle point and disease state.

14. The cell array of claim 3, wherein the array is an embryonic cell array, adult cell array, primary cell array, cell line array, tissue array, mammalian cell array, zoo array, personal cell array, genetically altered cell array, chemically treated cell array, or disease cell array.

15. The cell array of claim 3, wherein the cell array is a cancer cell array.

16. The cell array of claim 3, wherein at least the subset of the tube segments has an exposed upper transverse section of surface.

17. The cell array of claim 13, wherein cells contained in the different tube segments of the subset differ in species of origin.

18. The cell array of claim 13, wherein cells contained in the different tube segments of the subset differ in developmental origin, said developmental origin being selected from the group consisting of endodermal, mesodermal, and ectodermal origin.

19. The cell array of claim 13, wherein cells contained in the different tube segments of the subset differ in tissue origin.

20. A kit for simultaneously detecting the presence of a target polynucleotide or polypeptide in a multiplicity of cell types comprising a cell array of claim 16 in suitable packaging.

21. The cell array of claim 17, wherein said species of origin is selected from the group consisting of human, mouse, rat, fruit fly, worm, yeast and bacterium.

22. The cell array of claim 19, wherein said tissue origin is selected from the group consisting of blood, muscle, nerve, brain, heart, lung, liver, pancreas, spleen, thymus, esophagus, stomach, intestine, kidney, testis, ovary, hair, skin, bone, breast, uterus, bladder, spinal cord, and body fluids.

23. The cell array of claim 1, wherein each tube segment of the array has a maximum length in the range of about 0.01 micron to about 5 mm.

24. The cell array of claim 11, wherein each lumen has a transverse sectional area of about 0.01 mm to about 5 cm$^2$.

* * * * *

UNITED STATES PATENT AND TRADEMARK OFFICE
CERTIFICATE OF CORRECTION

PATENT NO.     : 6,406,840 B1
DATED          : June 18, 2002
INVENTOR(S)    : Ronghao Li and Jennie P. Mather It is certified that error appears in the above-identified patent and that said Letters Patent is hereby corrected as shown below:

<u>Column 32,</u>
Line 42, please delete "11" and insert therefor: -- 1 --.

Signed and Sealed this

Twenty-fifth Day of March, 2003

JAMES E. ROGAN
*Director of the United States Patent and Trademark Office*